US010738450B2

(12) United States Patent
Reichert et al.

(10) Patent No.: US 10,738,450 B2
(45) Date of Patent: Aug. 11, 2020

(54) TOILET RIM BLOCK AND RIM BLOCK CAGE

(71) Applicant: Henkel AG & Co. KGaA, Duesseldorf (DE)

(72) Inventors: Christian Reichert, Weingarten (DE); Uwe Trebbe, Duesseldorf (DE); Michael Horn, Duesseldorf (DE); Robert Stephen Cappleman, Duisburg (DE); Michael Voelker, Brueggen (DE)

(73) Assignee: Henkel AG & Co. KGaA (DE)

( * ) Notice: Subject to any disclaimer, the term of this patent is extended or adjusted under 35 U.S.C. 154(b) by 141 days.

(21) Appl. No.: 15/888,485

(22) Filed: Feb. 5, 2018

(65) Prior Publication Data

US 2018/0155909 A1 Jun. 7, 2018

Related U.S. Application Data

(63) Continuation of application No. PCT/EP2016/067782, filed on Jul. 26, 2016.

(30) Foreign Application Priority Data

Aug. 7, 2015 (DE) .......................... 10 2015 215 135

(51) Int. Cl.
*C11D 17/00* (2006.01)
*E03D 9/03* (2006.01)
(Continued)

(52) U.S. Cl.
CPC .............. *E03D 9/032* (2013.01); *A61L 2/232* (2013.01); *A61L 9/05* (2013.01); *C11D 3/10* (2013.01);
(Continued)

(58) Field of Classification Search
CPC ........................... C11D 17/056; C11D 17/0056
(Continued)

(56) References Cited

U.S. PATENT DOCUMENTS

| 4,460,490 A | 7/1984 | Barford et al. |
| 6,376,442 B1 * | 4/2002 | Perthuisot ................ C11D 3/50 264/148 |

(Continued)

FOREIGN PATENT DOCUMENTS

| DE | 4439677 A1 | 5/1996 |
| DE | 19856214 C1 | 3/2000 |

(Continued)

OTHER PUBLICATIONS

International Search Report PCT/EP2016/067779 Completed: Oct. 27, 2016; dated Nov. 8, 2016 4 pages.
(Continued)

*Primary Examiner* — Gregory E Webb
(74) *Attorney, Agent, or Firm* — Bojuan Deng

(57) ABSTRACT

A toilet rim block which consists of an outer cover and a core, and to a rim block cage including the toilet rim block. The outer cover includes a first composition and the core includes a second composition. Preferably, the first and the second compositions differ from each other by at least one of the following features: different active substances, different concentration but same active substance, and different viscosity. The outer cover partly encloses the core and the core protrudes on at least one face of the toilet rim block right to the surface as a pole and is exposed. The core is shaped such that the surface of the exposed area changes upon even wear of the surface of the toilet rim block, the surface of the exposed area of the core increasing upon even wear of the surface of the toilet rim block.

20 Claims, 4 Drawing Sheets

(51) Int. Cl.
*A61L 9/05* (2006.01)
*E03D 9/02* (2006.01)
*A61L 2/232* (2006.01)
*C11D 3/10* (2006.01)
*C11D 3/20* (2006.01)
*C11D 3/40* (2006.01)
*C11D 3/50* (2006.01)
*E03D 9/00* (2006.01)
*A61L 2/18* (2006.01)

(52) U.S. Cl.
CPC .............. *C11D 3/2086* (2013.01); *C11D 3/40* (2013.01); *C11D 3/50* (2013.01); *C11D 17/0056* (2013.01); *E03D 9/005* (2013.01); *E03D 9/02* (2013.01); *A61L 2/18* (2013.01); *A61L 2202/17* (2013.01); *E03D 2009/024* (2013.01); *E03D 2009/026* (2013.01)

(58) Field of Classification Search
USPC .................................................. 510/191, 192
See application file for complete search history.

(56) References Cited

U.S. PATENT DOCUMENTS

| | | |
|---|---|---|
| 6,806,244 B1 | 10/2004 | Waschenbach et al. |
| 6,863,830 B1 | 3/2005 | Muehlhausen et al. |
| 10,196,803 B2 | 2/2019 | Muelhausen et al. |
| 2012/0047640 A1* | 3/2012 | Warkotsch .............. E03D 9/032 4/223 |

FOREIGN PATENT DOCUMENTS

| | | |
|---|---|---|
| DE | 19925518 A1 | 12/2000 |
| DE | 10062262 A1 | 7/2002 |
| DE | 102004011256 A1 | 9/2005 |
| DE | 102008028138 A1 | 12/2009 |
| DE | 102008037723 A1 | 2/2010 |
| DE | 102010043848 A1 | 5/2012 |
| DE | 102012214898 A1 | 5/2014 |
| DE | 202010018282 U1 | 6/2015 |
| EP | 0791047 A1 | 8/1997 |
| EP | 1553162 A1 | 12/2004 |
| EP | 1836290 A1 | 9/2007 |
| WO | 2006070209 A1 | 6/2006 |
| WO | 2010018006 A1 | 2/2010 |
| WO | 2012062914 A1 | 5/2012 |

OTHER PUBLICATIONS

International Search Report PCT/EP2016/067781 Completed: Oct. 26, 2016; dated Nov. 3, 2016 4 pages.
International Search Report PCT/EP2016/067783 Completed: Oct. 28, 2016; dated Nov. 8, 2016 6 pages.
International Search Report PCT/EP2016/067782 Completed: Oct. 26, 2016; dated Nov. 8, 2016 6 pages.

* cited by examiner

TOILET RIM BLOCK AND RIM BLOCK CAGE

FIELD OF THE INVENTION

The present invention is in the field of toilet rim blocks and relates to a toilet rim block that consists of at least one mass and a core. The invention also relates to a rim block cage comprising a toilet rim block according to the invention.

BACKGROUND OF THE INVENTION

Toilet rim blocks comprising two masses are known, for example from EP0791047 B1. A toilet rim block is described therein, in which one mass is surrounded at least in part by a further mass. Since both masses comprise the same active ingredient in different concentrations, upon rinsing and complete transition to the inner mass, there is a change in the concentration of the active ingredient. However, this change is sudden, and a continuous change is not possible using this technology without significant effort.

DE 102008028138 A1 discloses coated toilet rim blocks, in which the compositions of the toilet rim block and the coating thereof are separated. When first used, e.g. at the time of the first flush, no active ingredient is dispensed from the toilet rim block into the flushing water, but rather from the coating of said block. It is thus possible to adjust optical properties of the toilet rim block. Furthermore, WO 2010018006 proposes coating the toilet rim blocks in order to adjust optical properties.

WO 2006070209 discloses cylindrical toilet rim blocks that comprise a core. Said blocks are used mainly as in-tank cleansing blocks and are intended to be permanently in water.

WO 2012062914 describes multilayer toilet rim blocks, in which the different layers can have different effects.

An essential feature of the embodiments known from the prior art is that the transition between the layers is sudden, in particular when the transition is intended to be an indicator of consumption. No solution has yet been found for achieving a continuous change in the dispensing of the active ingredient.

BRIEF SUMMARY OF THE INVENTION

This problem is solved by the toilet rim block disclosed herein. The present invention relates to a toilet rim block that consists of at least a casing and a core. The casing comprises a first composition and the core comprises a second composition. The first and the second composition preferably differ by at least one of the following features: different active ingredients, different concentration of the same active ingredient, or a different viscosity. The casing surrounds the core mass in part. The core projects, on at least one side of the toilet rim block, as a pole as far as the surface of the toilet rim block, and is thus exposed. Preferably, the profile of the core in the toilet rim block is such that the surface of the exposed face changes with uniform wear of the surface of the toilet rim block.

In this case, it is possible to dispense active ingredients into the flush simultaneously from the casing and from the core from the very start and in conjunction with a very wide variety of geometrical external shapes of the toilet rim block. In this case, the dispensing ratio of active ingredients from the casing and from the core can be specifically adjusted to the number of flushes. In particular, the dispensing ratio can be adjusted such that it can change continuously with the number of flushes. The change is preferably continuous.

Preferably, the initial situation on the undissolved toilet rim block is decisive for the change in the surface of the exposed face of the core and thus for the change in the active ingredient composition dispensed into the flush in each case. In other words, the initial situation is, preferably, the undissolved toilet rim block in the unused original state. Within the meaning of the invention, "exposed" means the bare surface.

Outer, for example full-surface, coatings of the toilet rim block which provide the unused toilet rim block with a shine for example can additionally be provided. Coatings of this kind are usually very thin, and therefore dissolve in the first flushes, preferably even in the first 3 flushes, particularly preferably even in the first flush. Accordingly, active ingredients actually begin to be dispensed into the flushing water only after said outer coating has dissolved. Therefore, for the purpose of the present invention, the initial situation for the undissolved toilet rim block is understood to be the toilet rim block without said outer coating.

In one embodiment of the invention, the surface of the exposed face of the core increases with uniform wear of the surface of the toilet rim block during ongoing use.

Viewed from outside the preferably spherical toilet rim block and towards the center of the toilet rim block, the core preferably forms a truncated cone having convex walls, the top face (the smaller face of the frustum) of the cone being a geometric shape that is projected onto the outer face of the toilet rim block, preferably the spherical surface thereof, which shape is preferably the projection of a circle, an ellipse, a polygon or a shape that differs slightly therefrom. A dome shape is an example of a cone of this kind.

For the undissolved toilet rim block, the area ratio of the exposed surface of the core to the exposed surface of the casing is preferably between 5% and 67%, particularly preferably between 10% and 38%.

It is also possible, but less preferable, for the toilet rim block to be totally covered by the core (99%-100% coverage) or by the casing in the unused original state of the toilet rim block. Specifically, the total coverage means that initially only one composition can be dispensed when the toilet rim block is undissolved.

After the toilet rim block has been partially used, the area ratio of the exposed surface of the core to the exposed surface of the casing is preferably between 1:3 and 1:1.

It is furthermore preferable for the toilet rim block to comprise a second pole that projects to the surface on the side of the toilet rim block opposite the first pole, and is thus exposed.

Preferably at least one, preferably the central, core portion is formed as a cylindrical segment. In particular for two-pole toilet rim blocks, the core can be produced having a distribution that is substantially symmetrical with respect to the two poles, provided that the central portion is cylindrical.

It is also preferable for the first pole and the second pole to be connected by a strand. It is preferable for the core to be integral. This results in a better time variation of the dispensing of the active ingredient as the toilet rim block is consumed.

According to a preferred embodiment of the invention, in particular in combination with two-pole toilet rim blocks, the casing surrounds the core in an annular manner. The core can thus extend through the center of the ring and open out on each side as the first and second pole.

In an alternative embodiment of the invention, the cross-sectional profile of the core has a cross-sectional enlargement between the first pole and the second pole.

The toilet rim block is preferably spherical. The sphericity is preferably between 0.8 and 1, i.e. substantially ball-shaped, particularly preferably between 0.85 and 1 and very particularly preferably between 0.9 and 1. According to a particularly preferred embodiment of the invention, a rim block cage comprises at least 2, preferably at least 3, spherical toilet rim blocks that are arranged in a row, it being further preferable for the poles of the toilet rim blocks to be arranged randomly. Random arrangement means that the toilet rim blocks included in the toilet rim block arrangement have different pole orientations. A rim block cage of this kind can be produced more cost-effectively since it is not necessary to orient the toilet rim blocks in advance. It has been found that spherical toilet rim blocks according to the invention mean that orientation in advance is not necessary in order to produce the desired dispensing ratio to the number of flushes. Of course, the toilet rim blocks can also be oriented, if a specific aesthetic form is desired, in particular if the core and the casing are different colors.

The sphericity $\Psi$ of a body K is the ratio of the surface of the body to the surface of a ball of the same volume:

$$\Psi = \frac{\pi^{\frac{1}{3}}(6V_p)^{\frac{2}{3}}}{A_p},$$

where Vp is the volume of the body and Ap is the surface of said body.

The almost ideal spherical shape of the toilet rim block achieves uniform rinsing of the toilet cleansing block such that the toilet rim block substantially maintains its ball shape even during and/or after the rinsing processes and corresponding wear of the toilet cleansing block.

The diameter of the spherical toilet rim block is preferably between 1 mm and 10 cm, preferably between 5 mm and 5 cm, particularly preferably between 1 cm and 3 cm.

The invention further relates to an associated method for producing a rotationally symmetrical toilet cleansing block, comprising the steps of
 a) mixing the ingredients for the core composition, and mixing the ingredients for the casing composition,
 b) co-extruding the at least two mixtures,
 c) cutting the extruded strand into portion pieces of a defined mass,
 d) shaping into rotationally symmetrical bodies such that the core projects, on at least one side of the toilet rim block, as a pole as far as the surface, and is thus exposed.

The shaping d) preferably takes place in a ball turning machine or in a press. A preferred ball turning machine is one comprising three rotating sections or rolls in which the strand can be inserted, and the strand is cut by the roll sections and shaped into a ball by reducing the distance between the rolls. The desired final geometry according to the invention is achieved by pressing the strand portion into a spherical space having an identical volume.

Steps a) and b) can also be combined, i.e. mixing the ingredients in the extruder. The method steps may be carried out at different temperatures, and therefore heating or cooling steps may be interposed between the steps. This is at the discretion of a person skilled in the art.

In a preferred embodiment, a further method step is carried out after one of steps b) or c), in which the extruded strand is provided with a lubricant. For this purpose, a sponge, in the form of a wheel, that is permanently filled with the lubricant is guided over the extruded strand such that lubricant is applied to all or part of the surface, preferably to between 10 and 40% thereof. In this case, adding the lubricant improves the subsequent ball forming. Suitable lubricants are in particular substances that are used for example as surfactants or rinsing regulators in formulations according to the invention. In this case, a lubricant selected from the group comprising dipropylene glycol, paraffins, non-ionic surfactants, polyethylene glycol and mixtures thereof, in particular dipropylene glycol, is particularly preferably used.

The method for producing the rim block cage comprises steps a) to d) described above, and further comprises:
 e) providing a plastics holder, preferably by means of an injection molding process;
 f) inserting the toilet rim block in the plastics holder;
 g) closing the plastics holder.

Preferably, the toilet rim blocks are temporarily stored in a container between steps d) and f). The container forms a kind of buffer, and it is thus possible to decouple the production of the toilet rim blocks from the production of the rim block cages. Preferably, the toilet rim blocks that are used in the cages come from at least two containers, the containers having stored toilet rim blocks having different compositions. A rim block cage can thus be produced that can dispense active ingredients from different toilet rim blocks having different compositions.

Composition

The first and the second composition preferably differ at least by including different active ingredients and/or by a different concentration of the same active ingredient, the active ingredients in question being selected from the following list: perfume, surfactant(s), dyes, rinsing regulators, bleaching agents, builders, acid or base, antimicrobial active ingredients, polymers. Particularly preferably, the active ingredients in question are selected from at least one of: perfume, surfactant(s), dyes. In the case of a toilet rim block in which the first and the second compositions differ by a different concentration of the same active ingredient, it is preferable for the core to comprise a higher concentration of said active ingredient. Preferably, the higher concentration in the core is at least 0.5 wt. % greater than in the casing. Furthermore, it is preferable for the active ingredient in the core to have a concentration that is between at least 1 wt. % and 10 wt. % higher than the concentration in the casing. The wt. % specification is always in relation to the overall composition of 100%. A concentration that is x wt. % higher means x percentage points more.

The rim block cage according to the invention comprising a toilet rim block can in addition be used in a method for cleaning and/or fragrancing and/or disinfecting flush toilets, such that the rim block cage filled with the toilet rim block is hung in the toilet bowl and, when the toilet flush is actuated, dissolved ingredients of the toilet rim block enter the flushing water and can there have their cleaning and/or fragrancing and/or disinfecting effect. The invention therefore furthermore relates to a method for cleaning and/or fragrancing and/or disinfecting flush toilets using a rim block cage according to the invention comprising a toilet rim block.

Substances that are also used as ingredients of cosmetic agents are designated in the following according to the International Nomenclature Cosmetic Ingredient (INCI) as appropriate. Chemical compounds have an English INCI designation, botanical ingredients are listed exclusively in Latin, in accordance with Linné, and what are known as common names such as "water", "honey" or "sea salt" are also specified in Latin. The INCI designations can be found in the International Cosmetic Ingredient Dictionary and Handbook—Seventh Edition (1997), which is published by The Cosmetic, Toiletry, and Fragrance Association (CTFA), 1101 17th Street, NW, Suite 300, Washington D.C. 20036, USA and contains over 9000 INCI designations and references to over 37,000 trade names and technical names, including the associated distributors from over 31 countries. The International Cosmetic Ingredient Dictionary and Handbook assigns the ingredients one or more chemical classes, for example Polymeric Ethers, and one or more functions, for example Surfactants—Cleansing Agents, which it then explains in greater detail and to which reference may also subsequently be made.

The expression CAS means that the following numerical sequence is a designation of the Chemical Abstracts Service.

In the scope of the present invention, unless otherwise stated, fatty acids and/or fatty alcohols and/or the derivatives thereof represent branched or unbranched carboxylic acids and/or alcohols and/or the derivatives thereof preferably having 6 to 22 carbon atoms, in particular 8 to 20 carbon atoms, particularly preferably 10 to 18 carbon atoms, most preferably 12 to 16 carbon atoms, for example 12 to 14 carbon atoms. The former are particularly preferred for ecological reasons, on account of the vegetable basis thereof, based on sustainable raw materials, but the teaching according to the invention is not restricted thereto. In particular, the oxo alcohols and the derivatives thereof which can be obtained according to Roelen's oxo synthesis for example and which preferably comprise 7 to 19 carbon atoms, in particular 9 to 19 carbon atoms, particularly preferably 9 to 17 carbon atoms, most preferably 11 to 15 carbon atoms, for example 9 to 11, 12 to 15 or 13 to 15 carbon atoms, can also be used correspondingly.

Perfume

The compositions preferably each include one or more fragrances, preferably in an amount of from 0.01 to 15 wt. %, in particular 1 to 11 wt. %, particularly preferably 1 to 8 wt. %. Preferably, the concentration in the casing is between 1 wt. % and 3 wt. %, and the concentration in the core is at least 0.5 wt. % higher, particularly preferably between 1.5 wt. % and 8 wt. %.

In this case, d-limonene can be included as a perfume component. In a particularly preferred embodiment, the toilet cleansing block according to the invention includes a perfume made up of ethereal oils (also referred to as essential oils). For example pine, citrus, jasmine, patchouli, rose, or ylang-ylang oil can be used as said oils within the meaning of the invention. Clary sage oil, chamomile oil, lavender oil, clove oil, melissa oil, mint oil, cinnamon leaf oil, lime blossom oil, juniper berry oil, vetiver oil, olibanum oil, galbanum oil, and labdanum oil, as well as orange blossom oil, neroli oil, orange peel oil, and sandalwood oil are also suitable.

In order to be perceptible, an odorant should be volatile, whereby in addition to the nature of the functional groups and the structure of the chemical compound, the molar mass also plays an important role. Therefore, most odorants possess molar masses of up to approximately 200 daltons, whereas molar masses of 300 daltons and above represent something of an exception. Due to the differing volatility of odorants, the odor of a perfume composed of multiple odorants varies over the course of vaporization, the odor impressions being divided into "top note", "middle note or body" and "end note or dry out."

Examples of semisolid odorants that can advantageously be used in the perfume oils within the scope of the present invention are essential oils such as angelica root oil, anise oil, arnica blossom oil, basil oil, bay oil, champaca blossom oil, abies alba oil, abies alba cone oil, elemi oil, eucalyptus oil, fennel oil, spruce needle oil, galbanum oil, geranium oil, ginger grass oil, guaiac wood oil, gurjun balsam oil, helichrysum oil, ho oil, ginger oil, iris oil, cajeput oil, calamus oil, chamomile oil, camphor oil, cananga oil, cardamom oil, cassia oil, pine needle oil, copaiba balsam oil, coriander oil, spearmint oil, caraway oil, cumin oil, lemon grass oil, musk seed oil, myrrh oil, clove oil, neroli oil, niaouli oil, olibanum oil, oregano oil, palmarosa oil, patchouli oil, balsam Peru oil, petitgrain oil, pepper oil, peppermint oil, allspice oil, pine oil, rose oil, rosemary oil, sandalwood oil, celery oil, star anise oil, thuja oil, thyme oil, verbena oil, vetiver oil, juniper berry oil, wormwood oil, wintergreen oil, ylang-ylang oil, hyssop oil, cinnamon oil, cinnamon leaf oil and cypress oil.

However, higher-boiling and solid odorants of natural or synthetic origin may also advantageously be used in the perfume oils, within the scope of the present invention, as semisolid odorants or odorant mixtures. These compounds include the compounds described below and mixtures thereof: Ambrettolide, α-amylcinnamaldehyde, anethole, anisaldehyde, anise alcohol, anisole, anthranilic acid methyl ester, acetophenone, benzyl acetone, benzaldehyde, benzoic acid ethyl ester, benzophenone, benzyl alcohol, borneol, benzyl acetate, α-bromostyrene, n-decyl aldehyde, n-dodecyl aldehyde, eugenol, eugenol methyl ether, eucalyptol, farnesol, fenchone, fenchyl acetate, geranyl acetate, geranyl formate, heliotropin, heptyne carboxylic acid methyl ester, heptaldehyde, hydroquinone dimethyl ether, hydroxycinnamaldehyde, hydroxycinnamyl alcohol, indole, irone, isoeugenol, isoeugenol methyl ether, isosafrole, jasmone, camphor, carvacrol, carvone, p-cresol methyl ether, coumarin, p-methoxyacetophenone, methyl n-amyl ketone, methyl anthranilic acid methyl ester, p-methyl acetophenone, methyl chavicol, p-methyl quinoline, methyl β-naphthyl ketone, methyl n-nonyl acetaldehyde, methyl n-nonyl ketone, muscone, β-naphthol ethyl ether, β-naphthol methyl ether, nerol, nitrobenzene, n-nonyl aldehyde, nonyl alcohol, n-octyl aldehyde, p-oxyacetophenone, pentadecanolide, β-phenyl ethyl alcohol, phenyl acetaldehyde dimethyl acetal, phenylacetic acid, pulegone, safrole, salicylic acid isoamyl ester, salicylic acid methyl ester, salicylic acid hexyl ester, salicylic acid cyclohexyl ester, santalol, skatole, terpineol, thymene, thymol, γ-undecalactone, vanillin, veratrum aldehyde, cinnamaldehyde, cinnamyl alcohol, cinnamic acid, cinnamic acid ethyl ester, and cinnamic acid benzyl ester.

More volatile odorants that can advantageously be used in the perfume oils within the scope of the present invention include in particular lower-boiling odorants of natural or synthetic origin, which may be used alone or in mixtures. Examples of more volatile odorants are alkyl isothiocyanates (alkyl mustard oils), butanedione, limonene, linalool, linalyl acetate and propionate, menthol, menthone, methyl-n-heptenone, phellandrene, phenylacetaldehyde, terpinyl acetate, citral and citronellal.

Surfactants

The toilet rim block according to the invention includes at least one non-ionic surfactant, a C12-22 fatty alcohol alkoxylate having a degree of ethoxylation of from 12 to 28 being included, as well as at least one alkylbenzene sulfonate and at least one olefin sulfonate. Said block can in addition include further surfactants.

Preferred alkylbenzene sulfonates are in particular those having approximately 12 C-atoms in the alkyl moiety, such as linear sodium C10-13 alkylbenzene sulfonate. Preferred olefin sulfonates have a carbon chain length of from 14 to 16. The toilet cleansing block according to the invention preferably includes from 10 to 70 wt. %, preferably 20 to 65 wt. %, particularly preferably 20 to 30 wt. % alkylbenzene sulfonate, and preferably 10 to 30 wt. %, preferably 15 to 30 wt. %, particularly preferably 15 to 25 wt. % olefin sulfonate.

Non-Ionic Surfactants

Further non-ionic surfactants can be included in addition to the C12-22 fatty alcohol alkoxylate having a degree of ethoxylation of from 12 to 28. Further suitable non-ionic surfactants within the scope of the invention can be alkoxylates, such as polyglycol ethers, fatty alcohol polyglycol ethers, alkylphenol polyglycol ethers, end-capped polyglycol ethers, mixed ethers and hydroxy mixed ethers and fatty acid polyglycol esters. Ethylene oxide/propylene oxide block copolymers, fatty acid alkanolamides and fatty acid polyglycol ethers can also be used. A further significant class of non-ionic surfactants that can be used according to the invention are the polyol surfactants and here in particular the glycol surfactants such as alkyl polyglycosides and fatty acid glucamides. The alkyl polyglycosides are particularly preferred, in particular the alkyl polyglucosides, and above all the fatty alcohol alkoxylates (fatty alcohol polyglycol ethers).

Preferred fatty alcohol alkoxylates are ethylene oxide (EO) and/or propylene oxide (PO)-alkoxylated, unbranched or branched, saturated or unsaturated C8-22 alcohols having a degree of alkoxylation of up to 30, preferably ethoxylated C12-22 fatty alcohol having a degree of ethoxylation of less than 30, preferably 12 to 28, in particular 20 to 28, particularly preferably 25, for example C16-18 fatty alcohol ethoxylates having 25 EO.

Alkly polyglycosides are surfactants that can be obtained by reacting sugars and alcohols according to the relevant methods of preparative organic chemistry, the mixture being one of monalkylated, oligomeric or polymeric sugars, depending on the type of production. The alkyl polyglucosides are preferred alkyl polyglycosides, the alcohol particularly preferably being a long-chain fatty alcohol or a mixture of long-chain fatty alcohols and branched or unbranched C8 to C18 alkyl chains and the degree of oligomerization (DP) of the sugars being between 1 and 10, preferably 1 to 6, in particular 1.1 to 3, most preferably 1.1 to 1.7, for example C8-10 alkyl-1.5-glucoside (DP of 1.5).

Fatty alcohol ethoxylates are preferably used in amounts of up to 20 wt. %, particularly preferably 4 to 12 wt. %, particularly preferably 7 to 9 wt. %. In addition, further non-ionic surfactants such as fatty acid monoalkanolamides and/or alkyl polyglycosides can be included in amounts of up to 10 wt. %.

Further Anionic Surfactants

The toilet rim block according to the invention can include aliphatic sulfates such as fatty alcohol sulfates, fatty alcohol ether sulfates, dialkyl ether sulfates, monoglyceride sulfates and aliphatic sulfonates such as alkane sulfonates, ether sulfonates, n-alkyl ether sulfonates, ester sulfonates and lignosulfonates as further anionic surfactants. Fatty acid cyanamides, sulfosuccinates (sulfosuccinic acid esters), in particular sulfosuccinic acid mono- and di-C8-C18-alkyl esters, sulfosuccinamates, sulfosuccinamides, fatty acid isethionates, acylaminoalkansulfonates (fatty acid taurides), fatty acid sarcosinates, ether carboxylic acids and alkyl (ether)phosphates, and α-sulfo fatty acid salts, acylglutamates, monoglyceride disulfates and alkyl ethers of glycerol disulfate can also be used within the scope of the present invention.

The fatty alcohol sulfates and/or fatty alcohol ether sulfates, in particular the fatty alcohol sulfates, are preferred within the scope of the present invention. Fatty alcohol sulfates are products of sulfation reactions on corresponding alcohols, while fatty alcohol ether sulfates are products of sulfation reactions on alkoxylated alcohols. A person skilled in the art generally understands alkoxylated alcohols to be the reaction products of alkylene oxide, preferably ethylene oxide, with alcohols, within the meaning of the invention preferably with long-chain alcohols. In general, n mol ethylene oxide and one mol alcohol results, depending on the reaction conditions, in a complex mixture of addition products having different degrees of ethoxylation. A further embodiment of the alkoxylation consists in using mixtures of the alkylene oxides, preferably the mixture of ethylene oxide and propylene oxide. The sulfates of low-ethoxylated fatty alcohols having from 1 to 4 ethylene oxide units (EO), in particular 1 to 2 EO, for example 1.3 EO, are preferred fatty alcohol ether sulfates.

The anionic surfactants are preferably used as sodium salts, but can also be included as other alkali or alkaline-earth metal salts, for example magnesium salts, and in the form of ammonium salts or mono-, di-, tri- or tetraalkylammonium salts, and in the case of the sulfonates, also in the form of their corresponding acids, e.g. dodecylbenzenesulfonic acid.

In addition to the types of surfactants mentioned thus far, the agent according to the invention can in addition also include cationic surfactants and/or amphoteric surfactants.

Suitable amphoteric surfactants are, for example, betaines of formula $(R^{iii})(R^{iv})(R_v)N^+CH_2COO^-$, in which $R^{iii}$ denotes an alkyl functional group, which is optionally interrupted by heteroatoms or heteroatom groups, having 8 to 25, preferably 10 to 21, carbon atoms, and $R^{iv}$ and $R^v$ denote identical or different alkyl functional groups having 1 to 3 carbon atoms, in particular $C_{10}$-$C_{18}$ alkyl dimethyl carboxymethyl betaine and $C_{11}$-$C_{17}$ alkyl amido propyl dimethyl carboxymethyl betaine.

Suitable cationic surfactants are, inter alia, the quaternary ammonium compounds of formula $(R^{vi})(R^{vii})(R^{viii})(R^{ix})N^+ X^-$, in which $R^{vi}$ to $R^{ix}$ denote four identical or different, and in particular two long-chain and two short-chain, alkyl functional groups, and X-denotes an anion, in particular a halide ion, for example didecyl dimethyl ammonium chloride, alkyl benzyl didecyl ammonium chloride and the mixtures thereof.

Further Ingredients

In addition to the components mentioned thus far, the toilet rim block according to the invention can include further ingredients that are usually used in toilet rim blocks, preferably selected from the group comprising acids, bases, salts, thickening agents, antimicrobial active ingredients, preservatives, complexing agents, polymers, dyes, fragrances, perfume boosters, fillers, builders, bleaching agents, corrosion inhibitors, rinsing regulators, enzymes, microorganisms, active ingredients for inhibiting limescale deposits, active ingredients for reducing dirt adhesion, active ingredients for improving workability, active ingredients for reducing adhesiveness, and mixtures thereof. Overall, no more than 60 wt. %, preferably 0.01 to 60 wt. %, in particular 0.2 to 15 wt. % further ingredients should be included.

Acids

Toilet rim blocks according to the invention can include one or more acids and/or the salts thereof in order to increase the power for cleaning limescale and urine deposits. The acids are preferably produced from sustainable raw materials. Therefore, in particular organic acids such as formic acid, acetic acid, citric acid, glycolic acid, lactic acid, succinic acid, adipic acid, malic acid, tartaric acid and gluconic acid, and mixtures thereof, are suitable as acids. In addition, however, the inorganic acids hydrochloric acid, sulfuric acid, phosphoric acid and nitric acid, or sulfamic acid and the mixtures thereof can also be used. The acids and/or the salts thereof selected from the group comprising citric acid, lactic acid, formic acid, the salts thereof, and mixtures thereof are particularly preferred. Said acids and/or salts are used in amounts of from 0.01 to 10 wt. %, particularly preferably 0.2 to 5 wt. %.

In a preferred embodiment, the composition in addition includes inorganic salts, preferably alkali- or alkaline-earth metal salts, in particular carbonates, sulfates, halides or phosphates, and mixtures thereof. Particularly preferably, sodium sulfate and/or sodium carbonate are used. In this case, sodium sulfate can be included in an amount of up to 60 wt. %, preferably from 0.01 to 60 wt. %, particularly preferably 20 to 60 wt. %, in particular 35 to 55 wt. %. Sodium carbonate and further salts can be included in an amount of up to 30 wt. %, preferably up to 10 wt. %, particularly preferably up to 5 wt. %.

Bases

Further alkalis can be included in compositions according to the invention. Bases from the group of the alkali- and alkaline-earth metal hydroxides and carbonates, in particular sodium carbonate or sodium hydroxide, are preferably used as bases in the compositions according to the invention. In addition, however, ammonia and/or alkanolamines having up to 9 C-atoms in the molecule, preferably the ethanolamines, in particular monoethanolamine, can also be used.

Antimicrobial Active Ingredients

Disinfection and sanitation are a particular form of cleaning. In a corresponding particular embodiment of the invention, the toilet cleansing block therefore includes one or more antimicrobial active ingredients, preferably in an amount of from 0.01 to 1 wt. %, preferably 0.02 to 0.8 wt. %, in particular 0.05 to 0.5 wt. %, particularly preferably 0.1 to 0.3 wt. %, most preferably 0.2 wt. %.

The terms "disinfection", "sanitation", "antimicrobial effect" and "antimicrobial active ingredient" have the conventional meaning thereof within the scope of the teaching according to the invention. Whereas disinfection, in the narrow sense, means the medical practice of killing, theoretically all, infection germs, sanitation is to be understood as eliminating, as far as possible all, germs, including saprophytic germs that are usually harmless to humans. In this case, the extent of the disinfection or sanitation depends on the antimicrobial effect of the composition used, which effect reduces as the content of antimicrobial active ingredient decreases or as the composition to be used becomes increasingly diluted.

For example antimicrobial active ingredients from the groups of the alcohols, aldehydes, antimicrobial acids and the salts thereof, carboxylic acid esters, acid amides, phenols, phenol derivatives, diphenyls, diphenyl alkanes, urea derivatives, oxygen and nitrogen acetals and methylals, benzamidines, isothiazoles and the derivatives thereof such as isothiazolins and isothiazolinones, phthalimide derivatives, pyridine derivatives, antimicrobial surface-active compounds, guanidines, antimicrobial amphoteric compounds, quinolines, 1,2-Dibromo-2,4-dicyanobutane, iodo-2-propynyl-butylcarbamate, iodine, iodophors, compounds that lose active chlorine, and peroxides are suitable according to the invention. Preferred antimicrobial active ingredients are preferably selected from the group comprising ethanol, n-propanol, i-propanol, 1,3-butanediol, phenoxyethanol, 1,2-propylene glycol, glycerol, undecylenic acid, citric acid, lactic acid, benzoic acid, salicylic acid, thymol, 2-Benzyl-4-chlorophenol, 2,2'-methylenebis(6-bromo-4-chlorophenol), 2,4,4'-trichloro-2'-hydroxydiphenyl ether, N-(4-chlorophenyl)-N'-(3,4-dichlorophenyl)urea, N,N'-(decane-1,10-diyldi-1-pyridyl-4-ylidene)bis(octylammonium) dichloride, N,N-bis(4-chlorophenyl)3,12-diimino-2,4,11,13-tetraazatetradecandiimidamide, antimicrobial quaternary surface-active compounds, guanidines and sodium dichloroisocyanurate (DCI, 1,3-dichloro-5H-1,3,5-triazine-2,4,6-trione sodium salt). Preferred antimicrobially acting surface-active quaternary compounds include an ammonium, sulfonium, phosphonium, iodonium or arsonium group. Furthermore, antimicrobially acting essential oils can also be used, which oils simultaneously fragrance the cleaning agent. Particularly preferred antimicrobial active ingredients are, however, selected from the group comprising salicylic acid, quaternary surfactants, in particular benzalkonium chloride, peroxo compounds, in particular hydrogen peroxide, alkali metal hypochlorite, sodium dichloroisocyanurate and mixtures thereof.

Preservatives

Toilet cleansing blocks according to the invention can also include preservatives. Substantially the substances mentioned under the antimicrobial active ingredients can be used as preservatives of this kind.

Complexing Agents

Complexing agents (INCI Chelating Agents), also referred to as sequestering agents, are ingredients that allow metal ions to form complexes and to become inactive, in order to prevent the disadvantageous effects of said ions on the stability or the appearance of the agent, for example cloudiness. In this case it is important to form complexes from the calcium and magnesium ions of the water hardness that are incompatible with many ingredients. However, forming complexes from ions of heavy metals such as iron or copper slows the oxidative decomposition of the finished agents. The complexing agents in addition assist the cleaning effect.

For example the following complexing agents, named in accordance with INCI, are suitable: Aminotrimethylene Phosphonic Acid, Beta-Alanine Diacetic Acid, Calcium Disodium EDTA, Citric Acid, Cyclodextrin, Cyclohexanediamine Tetraacetic Acid, Diammonium Citrate, Diammonium EDTA, Diethylenetriamine Pentamethylene Phosphonic Acid, Dipotassium EDTA, Disodium Azacycloheptane Diphosphonate, Disodium EDTA, Disodium Pyrophosphate, EDTA, Etidronic Acid, Galactaric Acid, Gluconic Acid, Glucuronic Acid, HEDTA, Hydroxypropyl Cyclodextrin, Methyl Cyclodextrin, Pentapotassium Triphosphate, Pentasodium Aminotrimethylene Phosphonate, Pentasodium Ethylenediamine Tetramethylene Phosphonate, Pentasodium Pentetate, Pentasodium Triphosphate, Pentetic Acid, Phytic Acid, Potassium Citrate, Potassium EDTMP, Potassium Gluconate, Potassium Polyphosphate, Potassium Trisphosphonomethylamine Oxide, Ribonic Acid, Sodium Chitosan Methylene Phosphonate, Sodium Citrate, Sodium Diethylenetriamine Pentamethylene Phosphonate, Sodium Dihydroxyethylglycinate, Sodium EDTMP, Sodium Gluceptate, Sodium Gluconate, Sodium Glycereth-1 Polyphosphate, Sodium Hexametaphosphate, Sodium Metaphosphate, Sodium Metasilicate, Sodium Phytate, Sodium Polydimethylglycinophenolsulfonate, Sodium Trimetaphosphate, TEA-EDTA, TEA-Polyphosphate, Tetrahydroxyethyl Ethylenediamine, Tetrahydroxypropyl Ethylenediamine, Tetrapotassium Etidronate, Tetrapotassium Pyrophosphate, Tetrasodium EDTA, Tetrasodium Etidronate, Tetrasodium Pyrophosphate, Tripotassium EDTA, Trisodium Dicarboxymethyl Alaninate, Trisodium EDTA, Trisodium HEDTA, Trisodium NTA and Trisodium Phosphate.

Polymers

The toilet rim block according to the invention can additionally include polymers. Said polymers can, for example, reduce calcification and the tendency to become resoiled.

Acrylic polymers, such as are commercially available from the company Rhodia under the trade name Mirapol, are preferred polymers in this case.

Fragrances and Dyes

The toilet rim block according to the invention can include one or more fragrances and/or one or more dyes (INCI Colorants) as further ingredients. In this case, both water-soluble and oil-soluble dyes can be used as dyes, it being important both to take into account the compatibility with further ingredients, for example bleaching agents, and that the dye used should not significantly affect the toilet ceramics, even after long-term use. The dyes are preferably included in an amount of from 0.0001 to 0.1 wt. %, in particular 0.0005 to 0.05 wt. %, particularly preferably 0.001 to 0.01 wt. %.

Builders

Water-soluble and/or water-insoluble builders can optionally be used in the toilet rim block according to the invention. In this case, water-soluble builders are preferred since they are generally less likely to form insoluble residues on hard surfaces. Conventional builders which may be added within the scope of the invention are low-molecular polycarboxylic acids and the salts thereof, homopolymeric and copolymeric polycarboxylic acids and the salts thereof, citric acid and the salts thereof, carbonates phosphates and silicates. The category of water-insoluble builders includes zeolites, which may also be used, as well as mixtures of the aforementioned builder substances.

Bleaching Agents

According to the invention bleaching agents can be added to the cleaning agent. Suitable bleaching agents include peroxides, peroxy acids and/or perborates, hydrogen peroxide being particularly preferred. In contrast, sodium hypochlorite is less suitable in the case of cleaning agents having an acidic formulation, on account of the release of poisonous chlorine gas vapor, but can be used in the case of alkaline cleaning agents. In some circumstances, a bleach activator may also be required in addition to the bleaching agent.

Corrosion Inhibitors

Suitable corrosion inhibitors are, for example, the following substances, named in accordance with INCI: Cyclohexylamine, Diammonium Phosphate, Dilithium Oxalate, Dimethylamino Methylpropanol, Dipotassium Oxalate, Dipotassium Phosphate, Disodium Phosphate, Disodium Pyrophosphate, Disodium Tetrapropenyl Succinate, Hexoxyethyl Diethylammonium, Phosphate, Nitromethane, Potassium Silicate, Sodium Aluminate, Sodium Hexametaphosphate, Sodium Metasilicate, Sodium Molybdate, Sodium Nitrite, Sodium Oxalate, Sodium Silicate, Stearamidopropyl Dimethicone, Tetrapotassium Pyrophosphate, Tetrasodium Pyrophosphate, Triisopropanolamine.

Rinsing Regulators

The substances referred to as rinsing regulators primarily control the consumption of the composition during use such that the intended service life is met. Solid long-chain fatty acids such as stearic acid, but also salts of such fatty acids, fatty acid ethanolamides such as coconut fatty acid monoethanolamide, or solid polyethylene glycols such as those having molecular weights of between 10000 and 50000 are preferably suitable as regulators.

Active Ingredients for Reducing Adhesiveness

In order to improve the workability when producing the toilet rim block according to the invention, an active ingredient can be used to reduce the adhesiveness. Thus, adding dolomite powder or titanium dioxide powder having a fine particle size distribution improves the working behavior when forming balls and significantly reduces wear and adhesiveness.

The results using active ingredients of this kind are better than using other conventional measures, such as coating the balls with a sliding agent, powdering or coating the section rolls with Teflon.

Enzymes

The composition can also include enzymes, preferably proteases, lipases, amylases, hydrolases and/or cellulases. Said enzymes can be added to the composition according to the invention in any enzyme form established in the prior art. These include solutions of the enzymes, advantageously as concentrated as possible, dry and/or mixed with stabilizers. Alternatively the enzymes can also be encapsulated, for example through spray-drying or extrusion of the enzyme solution together with a preferably natural polymer or in the form of capsules, for example those in which the enzymes are enclosed in a set gel, or in those of the core-shell type in which an enzyme-containing core is coated with a water-, air-, and/or chemical-impermeable protective layer. In the case of overlaid layers, other active ingredients, such as stabilizers, emulsifiers, pigments, bleaching agents, or dyes, can be additionally applied. Such capsules are applied using inherently known methods, for example through shaking or roll granulation or in fluidized bed processes. Such granulates are advantageously low in dust, for example due to the application of polymeric film-formers, and stable in storage due to the coating.

Furthermore, enzyme stabilizers can be present in enzyme-containing compositions in order to protect an enzyme included in a composition according to the invention against damage, for example inactivation, denaturation, or decomposition caused, for example, by physical influences, oxidation, or proteolytic cleavage. Depending in each case on the enzyme used, particularly suitable enzyme stabilizers are: benzamidine hydrochloride, borax, boric acid, boronic acid or the salts or esters thereof, in particular derivatives having aromatic groups, such as substituted phenylboronic acids or the salts or esters thereof; peptide aldehydes (oligopeptides having a reduced C-terminus), alkanolamines such as mono-, di- and tri-ethanol and -propanolamine and the mixtures thereof, aliphatic carboxylic acids up to $C_{12}$, such as succinic acid, other dicarboxylic acids or salts of the mentioned acids; end-capped fatty acid amide alkoxylates; low aliphatic alcohols and in particular polyols, for example glycerol, ethylene glycol, propylene glycol or sorbitol; and reducing agents and antioxidants such as sodium sulfite and reducing sugars. Further suitable stabilizers are known from the prior art. Preferably, combinations of stabilizers are used, for example the combination of polyols, boric acid and/or borax, the combination of boric acid or borate, reducing salts and succinic acid or other dicarboxylic acids, or the combination of boric acid or borate with polyols or polyamino compounds and with reducing salts.

In a particularly preferred embodiment of the invention, the core and casing are different colors. Furthermore, particularly preferably, the core and casing are each a homogenous color. The color difference between the color of the casing and of the core ($\Delta E^*_{ab}$) is preferably greater than 3 in the CIE 1976 (L, a*, b*) color coordinate system. $\Delta E^*_{ab} = \sqrt{(L^*_2-L^*_1)^2+(a^*_2-a^*_1)^2+(b^*_2-b^*_1)^2}$ Alternatively or in addition, it is preferable for at least one color, preferably both, of the core and the casing to have a colorfulness (chroma) of between 20% and 99%, preferably between 30% and 95%.

Individually or preferably combined, the color settings according to the invention significantly improve the ability of the user of the toilet rim block to identify the degree of consumption. This is because the mutually contrasting effect of the elements make observation easier.

In an alternative variant of the invention, the color difference between the color of the casing and of the core ($\Delta E^*_{ab}$) is preferably less than 10, preferably less than 3, in the CIE 1976 (L, a*, b*) color coordinate system. In this case, it is preferable for the core to have different active ingredients and/or a different concentration of the same active ingredient compared to the casing. The user does not notice when the casing has been used up, and can have the impression that the toilet rim block consists of a single active ingredient composition. Nonetheless, a changed active ingredient composition of the core can at least in part compensate for the functionality and the effect, for example, of the toilet rim block in the event of heavy wear.

In the present description, the color features relate to the CIE 1976 color coordinate system. If an illuminant is required, the D65, or an approximation thereof that can be used in the conventional manner, is used.

Device

The present invention also provides a device that comprises a toilet rim block as described herein, and a retaining means for holding the toilet rim block on the toilet bowl. The device is preferably a rim block cage.

Rim Block Cage

According to the invention a rim block cage is provided, comprising at least one toilet rim block according to the invention. The rim block cage can preferably also comprise at least two, particularly preferably at least three toilet rim blocks according to the invention. The toilet rim blocks each comprise at least one polar cap and are arranged together in a regular or irregular manner. The irregular arrangement is preferred on account of the simpler production method. The regular arrangement is also significant, however, in particular on account of the aesthetic form, in particular if the pole and casing are different colors. The toilet rim blocks of the rim block cage are preferably rotationally symmetrical, more preferably spherical.

The rim block cage according to the invention is suitable for dispensing compositions into a toilet bowl. Said cage comprises a receptacle that is to be arranged in the toilet bowl, it being possible to fasten the receptacle to the toilet bowl. The receptacle comprises a first chamber that receives at least one toilet rim block. The receptacle preferably further comprises a second chamber that receives a second toilet rim block. Preferably at least one, preferably all, of the toilet rim blocks are separated from the base of the chambers by supporting means. At least one, preferably all, of the chambers in each case dispense the compositions into the toilet bowl when flushing water flows over or through said chambers. The rim block cage is designed such that, when flushing water flows thereover, the flushing water also comes into contact with the toilet rim block, and the flushing water enriched with active ingredient preparation can emerge from the rim block cage. For example inlet and outlet openings, water distribution elements and other means can be provided for this purpose. Embodiments will be described with reference to the drawings.

The rim block cage comprising the toilet rim block(s) is preferably closed such that it cannot be opened. It is thus not possible to reach the toilet rim block(s) without applying significant force and deforming the rim block cage.

The rim block cage is preferably transparent. A user can thus identify not only the color but also the shape of the toilet rim block.

BRIEF DESCRIPTION OF THE DRAWINGS

List of Figures

DETAILED DESCRIPTION OF THE INVENTION

Figure 1:
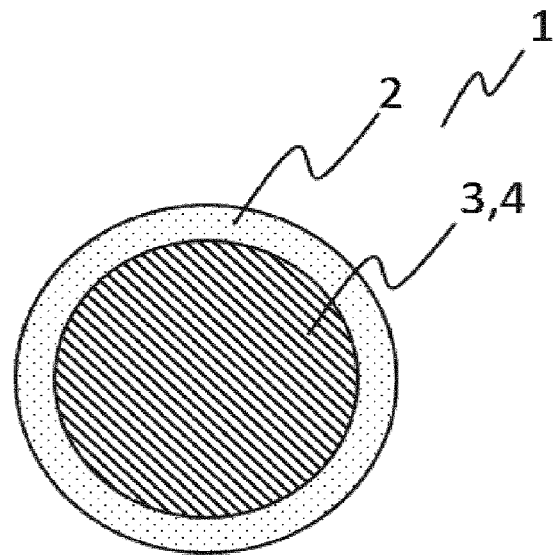
FIG. 1 is a plan view of the pole of a toilet rim block that is not in accordance with the invention.
Figure 2:
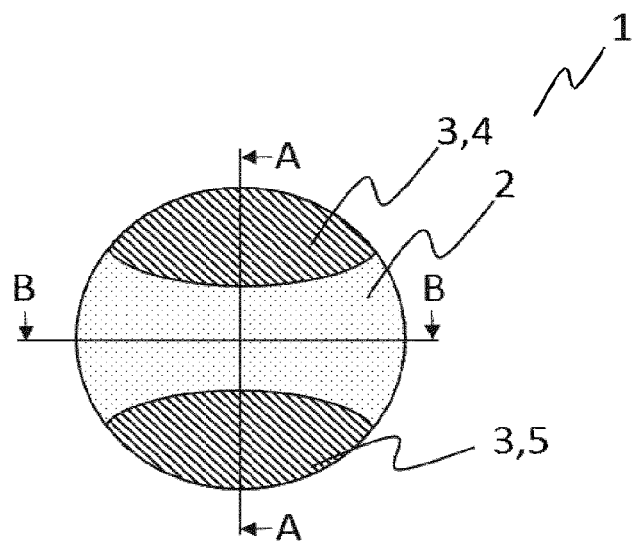
FIG. 2 is a side view of a toilet rim block that is not in accordance with the invention.
Figure 3:
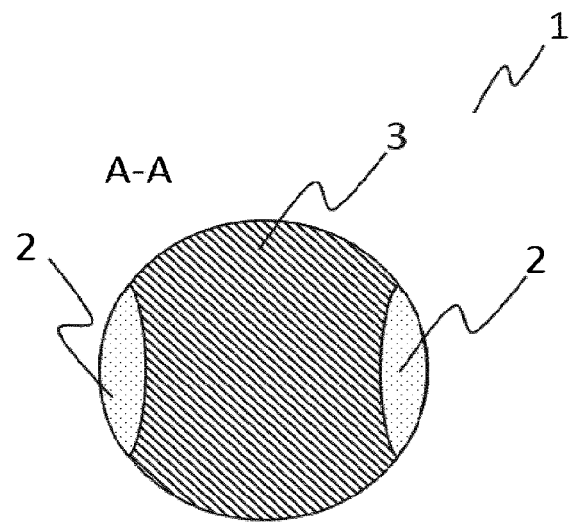
FIG. 3 shows a cross section of the toilet rim block from FIG. 2 in the direction A-A.
Figure 4:
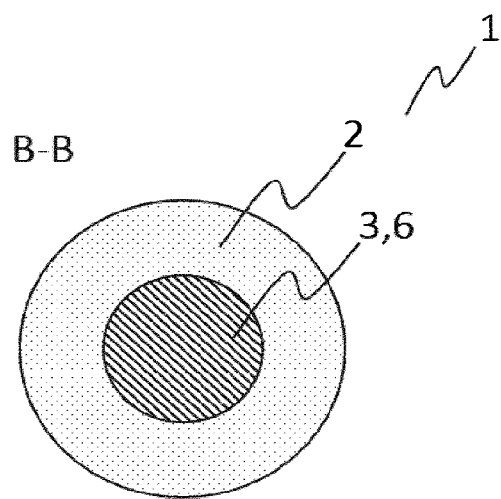
FIG. 4 shows a cross section of the toilet rim block from FIG. 2 in the direction B-B.

FIGS. 1 to 5 are not in accordance with the invention, but include many features which help to explain the invention.

In an example, the toilet rim block 1 comprises the casing 2 and the core 3. The core 3 forms a pole 4 which is visible in the plan view according to FIG. 1. The first pole 4 and the second pole 5 are visible in the side view according to FIG. 2. The core 3 is surrounded by the casing 2. The casing 2 is annular, as can be seen in the cross-sectional view A-A having an approximately elliptical cross section for example, and in the cross-sectional view B-B as a circular ring. The pole 4 and/or the pole 5 can be more or less pronounced in each case. This allows predefined, controlled release of active ingredients over the temporal progression. The diameter of the segment 6 can also be smaller or larger. Instead of a cylindrical portion of the segment 6, said segment can also have a different geometry.

Comparative Example

Toilet rim blocks were produced having the following compositions and used as reference:

|  | E1 |
|---|---|
| $C_{10-13}$ lin. Alkylbenzene sulfonate-Na | 26 |
| Fatty alcohol sulfate-Na | — |
| $C_{12}$ fatty alcohol sulfate-Na | – |

-continued

|  | E1 |
| --- | --- |
| C$_{14-16}$ olefin sulfonate-Na | 18 |
| C$_{16-18}$ fatty alcohol ethoxylate 25 EO | 8 |
| Cellulose | — |
| Trisodium citrate dihydrate | 1 |
| Sodium sulfate | to make up |
| Sodium carbonate | — |
| C$_{12-18}$ fatty acid monoethanolamide | — |
| Sodium silicate | — |
| Perfume | 4.5 |
| Dye | + |

The perfume composition used was composed as follows:

| Dosage Wt. % | Name | CAS no. |
| --- | --- | --- |
| 12.16 | dipropylene glycol | 25265-71-8 |
| 8.51 | dihydromyrcenol | 18479-58-8 |
| 7.30 | terpineol | 8000-41-7 |
| 4.86 | linalyl acetate | 115-95-7 |
| 3.65 | lemon oil messina | 84929-31-7 |
| 3.65 | agrunitrile | 51566-62-2 |
| 3.65 | orange oil sweet, Ital. | 8028-48-6 |
| 3.65 | otbcha | 88-41-5 |
| 3.65 | styrallyl acetate | 93-92-5 |
| 3.65 | linalool | 78-70-6 |
| 2.43 | aldehyde c-08 | 124-13-0 |
| 2.43 | alcohol c-08 | 111-87-5 |
| 2.43 | allyl amyl glycolate | 67634-00-8 |
| 2.43 | benzyl acetate | 140-11-4 |
| 2.43 | hedione | 24851-98-7 |
| 1.52 | linalool oxide | 1365-19-1 |
| 1.52 | lemonile | 61792-11-8 |
| 1.52 | *bromelia* | 93-18-5 |
| 1.52 | yara yara | 93-04-9 |
| 1.52 | aldehyde c-10 | 112-31-2 |
| 1.51 | aldehyde c-14 (so-called) | 104-67-6 |
| 1.50 | benzyl acetone | 2550-26-7 |
| 1.50 | acedyl | 54830-99-8 |
| 1.50 | propidyl | 68912-13-0 |
| 1.50 | isobornyl acetate | 125-12-2 |
| 1.50 | terpinolene 30 | 586-62-9 |
| 1.50 | lilial, lysmeral | 80-54-6 |
| 1.50 | citronellol pure | 106-22-9 |
| 1.50 | geraniol pure | 106-24-1 |
| 1.50 | nerol standard | 106-25-2 |
| 1.50 | phenethyl alcohol | 60-12-8 |
| 1.50 | geranyl acetate | 16409-44-2 |
| 1.50 | hexyl cinnamaldehyde (alpha) | 101-86-0 |
| 1.50 | isoraldeine 70 | 1335-46-2 |
| 1.50 | beta-ionone synth. | 14901-07-6 |
| 1.50 | iso e super | 54464-57-2 |
| 1.50 | ethylene brassylate | 105-95-3 |

The composition was mixed, subsequently extruded to form a strand, cut, and shaped into balls in a forming die. The final diameter of every ball was 25.4 mm.

Example

Toilet rim blocks were produced as follows. A first composition A was provided, as in the reference example, the only difference being that the perfume concentration was changed from 4+/−0.5 to 5.5+/−0.5. A second composition B was provided, as in the reference example, the only difference being that the perfume concentration was changed from 4+/−0.5 to 2.5+/−0.5. As in the comparative example, the compositions were in each case mixed. The mixture was then extruded to form a coaxial strand, comprising composition A as the inner strand and composition B as the outer strand. An extruder was used for this purpose. The coaxial, cylindrical strands had an outer diameter of 20.5 mm and an inner strand diameter of 7.3 mm. The strand was cut into cylinders of 26.36 mm in length, the cylinders each being shaped into a ball. The final diameter of every ball was 25.4 mm.

Comparative Tests

Balls from the example and from the comparative example were used in identical rim block cages and flushed in a test chamber in each case. The test chambers have an identical structure and are separated from one another so that there is no exchange of air between the chambers. Each test chamber additionally comprises a toilet bowl, and is rinsed by a constant airflow. The test chambers are located in a space (measuring space) specifically designed for the test chambers, which space is odorless, can be ventilated well and can optionally be subjected to forced ventilation by means of an activated carbon filter. The volume fraction of carbon dioxide in the measuring space is less than 0.15 vol. %, the air exchange rate is at least 4.4 m3/h per person. The temperature in the measuring space is 20° C. and is constant during measuring. The measuring space is not exposed to any direct solar radiation, and other interfering sources of light and noise are minimized as far as possible. All the devices that are associated with the test chamber must be odorless. The odor intensity is assessed by at least 20 testers, with generally equal numbers of men and women, trained in odors, being employed, who are all at least 16 years old. At the time the compounds are assessed, the testers are not influenced by interfering factors such as contact with perfumes, food, other natural stimulants or by colds or allergies.

The rim block cages were hung in identical positions in the toilet bowls, and each toilet bowl was flushed out a times per hour. Each flush used 6 liters of water. The testers made the measurements at 4, 72, 96, 120, 144, 168 and 172 hours. To carry out the assessment, the tester opens the window, positions their head in the interior of the test chamber, carries out the smell test, withdraws their head again and then closes the window.

The testers had the clear impression that the fragrance strength of the example was greater than in the comparative example. The user perceives that the fragrance has increased, compared to the comparative example, after just 72 hours. Since the core was exposed, the initial difference from the comparative example was small; at the start the user perceived a loss of just 24%, but this was made up for surprisingly quickly. Surprisingly, the user results were such that the toilet rim blocks and rim block cages emitted a stronger fragrance than the reference over the entire usage time, although the amount of perfume used is identical.

Example 2

Toilet rim blocks according to the invention were produced as follows. A first composition A was provided, as in the reference example, the only difference being that the perfume concentration was changed from 4+/−0.5 to 5.5+/−0.5. A second composition B was provided, as in the reference example, the only difference being that the perfume concentration was changed from 4+/−0.5 to 2.5+/−0.5. As in the comparative example, the compositions were in each case mixed. The mixture was then extruded to form a coaxial strand, comprising composition A as the inner strand and composition B as the outer strand. An extruder was used for this purpose. The coaxial, cylindrical strands had an outer diameter of 20.5 mm and an inner strand diameter of 7.3 mm. The strand was cut into cylinders of 26.36 mm in length. The cylinders were pressed by two rams, each having a radius of the ram surface of 12.7 mm over an end distance of 80% of the original strand portion length. The pressed parts were each shaped into a ball. The final diameter of every ball was 25.4 mm.

Figure 5:
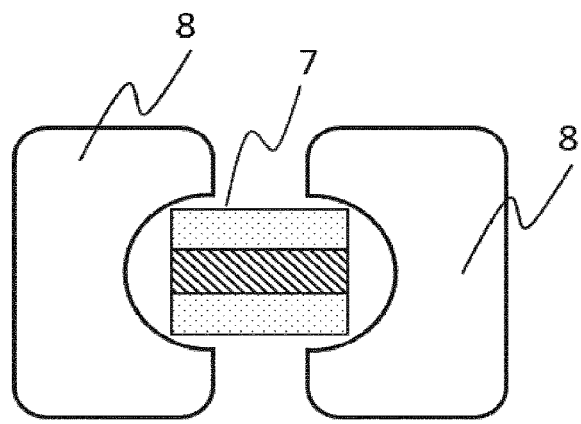
FIG. 5 is a cross-sectional view of the pressing process before and after pressing.
Figure 5:
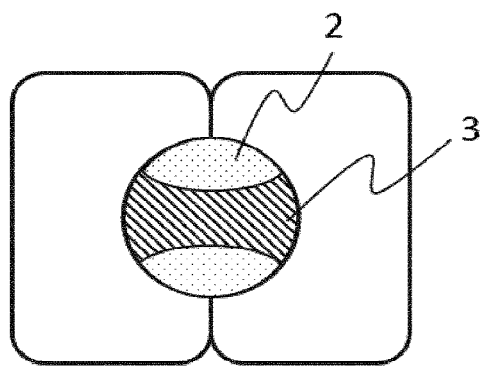

The essential part of a method is shown, in cross section, in FIG. 5. A co-extruded strand portion 7 is placed in a press 8. The final shape of the press 8 is a ball having an identical volume to the strand portion 7. The strand portion is shaped into a ball according to the invention by the cavities of the press 8 being brought together and the final shape thus being achieved.

A toilet rim block according to the invention is, for example, produced from a co-extruded strand portion. The strand portion is pressed, by two convex rams, the ram surface radius of which in each case approximately corresponds to the radius of the strand, between the cutting sides, and is only then processed by a ball turning machine.

Figure 7:
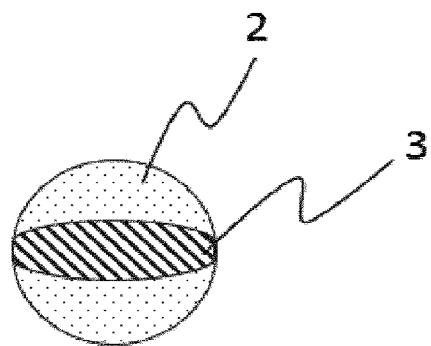
FIG. 7 shows a cross section of the toilet rim block that is not in accordance with the invention, after shaping.

FIG. 7 shows a cross section of a toilet rim block according to the invention. The toilet rim block is spherical, the core (3) is exposed on both sides. The profile of the core is such that the surface of the exposed face increases with uniform wear of the surface of the toilet rim block (1). A comparative sample was produced as a co-extruded cylinder, identical to the sample according to the invention except that the toilet rim block was not shaped into a ball; the core remained a regular cylinder. Surprisingly, it was found that the test subjects perceived the consumption and wear of the toilet rim block much more markedly in the case of different colors between the core and the casing than in the comparative sample.

Figure 6:
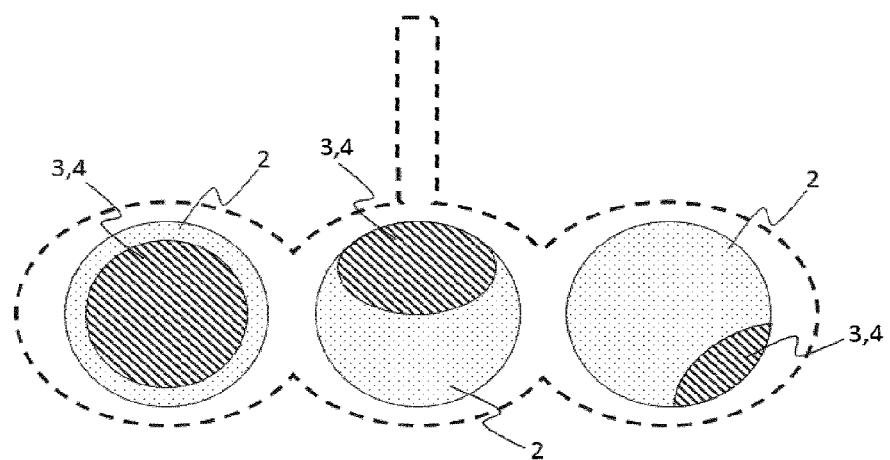
FIG. 6 shows a cross section of a rim block cage comprising 3 toilet rim blocks.

FIG. 6 shows a rim block cage by way of example. FIG. 6 shows 3 toilet rim blocks that each comprise a casing 2 and a pole 4. The toilet rim blocks are shown in the rim block cage that is shown from the front, by dashed lines and comprising a hanger. The cage is shown schematically so that the toilet rim blocks are more clearly visible. The toilet rim blocks are arranged in an irregular manner relative to one another, since each pole 4 faces in a different direction. In an example in accordance with the invention, the pole 4, in the unused state, is in each case somewhat smaller than can be seen in FIG. 6.

What is claimed is:

1. A toilet rim block consisting of at least a casing and a core,
   the casing comprising a first composition and the core comprising a second composition,
   the first and the second composition differing by at least one of the following features: different active ingredients, different concentration of the same active ingredient, different viscosity;
   the casing and the core cooperatively defining an outer surface of the toilet rim block, the outer surface being substantially ball-shaped;
   the casing surrounding the core in part,
   the core projecting on at least one side of the toilet rim block, as at least one pole, as far as the outer surface and thus defining at least one exposed face of the core that is surrounded by an exposed surface of the casing, wherein a profile of the core tapers through the toilet rim block such that a proportion of the at least one exposed face of the core to the exposed surface of the casing changes gradually with uniform wear of the outer surface of the toilet rim block.

2. The toilet rim block according to claim 1, wherein an area ratio of the at least one exposed face of the core to the exposed surface of the casing is between 5% and 67%.

3. The toilet rim block according to claim 1, wherein an area ratio of the at least one exposed face of the core to the exposed surface of the casing is between 10% and 38%.

4. The toilet rim block according to claim 1, wherein, when the toilet rim block has been partially dissolved, an area ratio of the at least one exposed face of the core to the exposed surface of the casing is between 1:3 and 1:1.

5. The toilet rim block according to claim 1, wherein at least one portion of the core is a cylindrical segment.

6. The toilet rim block according to claim 5, wherein a central portion of the core is the cylindrical segment.

7. The toilet rim block according to claim 1, wherein the core comprises a second pole that projects to the outer surface on the side of the toilet rim block opposite the first pole, and is thus exposed.

8. The toilet rim block according to claim 7, wherein the first pole and the second pole are connected by a core.

9. The toilet rim block according to claim 7, wherein a cross-sectional profile of the core through the first pole, the second pole, and the core has a cross-sectional enlargement between the first pole and the second pole.

10. The toilet rim block according to claim 1, wherein the toilet rim block is spherical.

11. The toilet rim block according to claim 1, wherein the casing surrounds the core in an annular manner.

12. The toilet rim block according to claim 1, wherein the first and the second composition differ by a different concentration of the same active ingredient, wherein the core has a concentration of an active ingredient that is at least 0.5 wt. % higher.

13. The toilet rim block according to claim 1, wherein the first and the second composition differ by a different concentration of the same active ingredient, wherein the core has a concentration of an active ingredient that is at least 1 wt. % to 10 wt. % higher.

14. A rim block cage comprising at least two toilet rim blocks according to claim 1.

15. A rim block cage comprising at least three toilet rim blocks according to claim 14.

16. The rim block cage according to claim 14, wherein the toilet rim blocks are rotationally symmetrical.

17. The rim block cage according to claim 14, wherein the toilet rim blocks are arranged with the at least one pole of each facing in different directions relative to one another.

18. The rim block cage according to claim 14, wherein the toilet rim blocks are rotationally spherical.

19. The toilet rim block of claim 1, wherein the core projects on a first side as a first pole and projects on a second side as a second pole, wherein the first pole and the second pole are connected via an interior segment; and
   wherein the profile of the core is symmetrical with respect to the first pole and the second pole.

20. The toilet rim block of claim 19, wherein the profile of the core tapers down in width from the first pole to the interior segment; and
   wherein the profile of the core tapers down in width from the second pole to the interior segment.

* * * * *